United States Patent [19]

Rogan

[11] Patent Number: 5,849,492

[45] Date of Patent: Dec. 15, 1998

[54] METHOD FOR RAPID IDENTIFICATION OF PROKARYOTIC AND EUKARYOTIC ORGANISMS

[75] Inventor: Peter K. Rogan, Lebanon, Pa.

[73] Assignee: Phylogenetix Laboratories, Inc., Pittsburgh, Pa.

[21] Appl. No.: 744,722

[22] Filed: Oct. 29, 1996

Related U.S. Application Data

[63] Continuation of Ser. No. 203,056, Feb. 28, 1994, abandoned.
[51] Int. Cl.$^6$ .............................. C12Q 1/68; C07H 21/02
[52] U.S. Cl. ................................................ 435/6; 536/23.1
[58] Field of Search .......................... 435/6, 91.2; 935/77, 935/70; 536/23.1

[56] References Cited

PUBLICATIONS

Lane et al, PNAS 82:6955–6959, 1985.
Bottger, FEMS Microbiol. Letters 65:171–176, 1989.
Naito et al, J. Forensic Sciences 37:396–403, 1992.
Schneider et al, Nucleic Acid Res 18:6097–6100, 1990.

*Primary Examiner*—Eggerton A. Campbell
*Attorney, Agent, or Firm*—Reed Smith Shaw & McClay LLP

[57] ABSTRACT

A method is described for retrieval of phylogenetically informative DNA sequences which comprise searching for a highly divergent segment of genomic DNA surrounded by two highly conserved segments, designing the universal primers for PCR amplification of the highly divergent region, and amplifying the genomic DNA by PCR technique using universal primers.

5 Claims, 9 Drawing Sheets

```
              10         20         30         40
    Hum  -----GTCCG GTGAGCTCTC GCTGGCCCTT GAAAATCCGG GGGAG
    Lem  --GGTGTCCG GTGCGCCCCC GGCGGCCCTT GAAAATCCGG AGGAC
  Mrace  ------TCTG GTGCATTCAC AACGATCCTT GAAAATCCAA GGGAA
   Rice  --GGTGTCCG GTGCGCCCCC GGCGGCCCTT GAAAATCCGG AGGA-
  Slime  --------GC GGTCTCCTTC CGTTGCCCTA GAAAGCTGG CAGAT
    Tom  --GGTGTCCG GTGCGCTCCC GGCGGCCCTT GAAAATTCCG GAGGA
   Worm  GTGGTGTCTC GTGCTCTTTG AACGGCCCTT AAAACACCAA GGGAG
   Xlrn  -GGCGTCCGG TGAGCTTCTC GCTGGCCCTT GAAAATCCGG GGGAG
  Yeast  --TGGCTCCG GTGCGCTTGT GACGGCCCGT GAAAATCCAC AGGA- 50         60         70         80         90
    Hum  AGG-- ----GTGTAA ATCTC-GCGC CGGGCCGTAC CCATATCCGC
    Lem  CG--- ----AGTG-- CCGCCCGCGC CCGGTCGTAC TCATAACCGC
  Mrace  A---- -----GAATA ATTTTCTCGC CTAGTCGTAC TCATAACCGC
   Rice  ----- ---CCGAGTA CCGTCCACGC CCGGTCGTAC TCATAACCGC
  Slime  GGGTG AAACGTGTTG TCCTTCG-GT TGAACCGTAC CTA-ATCCGC
    Tom  CCGAA TGCCGT---- ---TCCACGC CCGGTCGTAC TCATAACCGC
   Worm  GCTAT -------TAA TT---TGCAC TCAATCGTAC CGATATCCGC
   Xlrn  AGG-- ----GTGTAA ATCTCTGCGC CGGGCCGTAC CCATATCCGC
  Yeast  ----- ---AGGAATA GTTTTCATGC TAGGTCGTAC TGATAACCGC 100        110        120        130
    Hum  AGCAGGTCTC CAAGGTGAAC AGCCTCTGGC ATGTTGGAAC AATGT
    Lem  ATCAGGTCTC CAAGGTGAAC AGCCTCTGG- TCGATGGAAC AATGT
  Mrace  AGCAGGTCTC CAAGGTGAAA AGCCTCTAG- TTGATAGAAC AATGT
   Rice  ATCAGGTCTC CAAGGTGAAC GACCTCTGGC -CAATGGAAG AATGT
  Slime  AGCAGGTCTC CAAGATGAGC AGTCTCTGGC GCATAGAACA AAGTA
    Tom  ATCAGGTCTC CAAGGTGAAC AGCCTCTGG- TCGATGGAAC AATGT
   Worm  ATTAGGTCTC CAAGGTGAAC AGCCTCTAG- TCGATAGAAT AATGT
   Xlrn  AGCAGGTCTC CAAGGTGAAC AGCCTCTGGC ATGTTAGAAC AATGT
  Yeast  AGCAGGTCTC CAAGGTGAAC AGCCTCTAG- TTGATAGAAT AATGT 140        150        160        170
    Hum  AGGTA AGGGAAGTCG GCAAGCCGGA TCCGTAACTT CGG
    Lem  AGGCA AGGGAAGTCG GCAAAATGGA TCCGTAACTT CGG
  Mrace  AGATA AGGGAAGTCG GCAAAATAGA TCCGTAACTT CGG
   Rice  AGGCA AGGGAAGTCG GCAAAACGGA TCCGTAACTT CGG
  Slime  GCGTA AGGGAATTCG GCAAGCCGGA TTCGTAACTT CGG
    Tom  AGGCA AGGGAAGTCG GCAAAATGGA TCCGTAACTT CGG
   Worm  AGGTA AGGGAAGTCG GCAAACTAGA TCCGTAACTT CGG
   Xlrn  AGGTA AGGGAAGTCG GCAAGTCAGA TCCGTAACTT CGG
  Yeast  AGATA AGGGAAGTCG GCAAAATAGA TCCGTAACTT CGG
```

FIG. 1

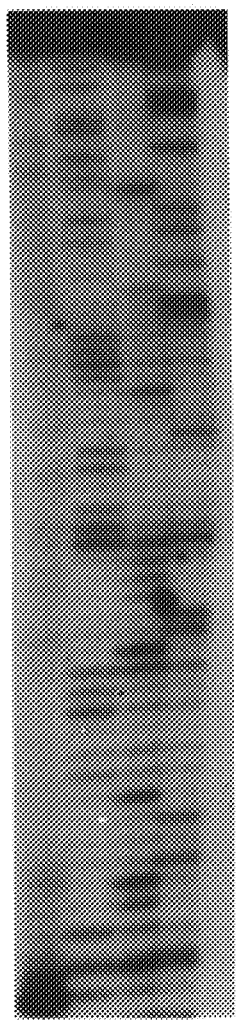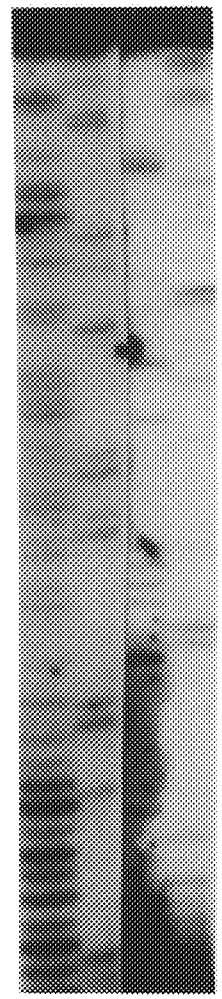
FIG. 6

(A)

| Accession Number | Locus Name | Latin name | Sequence designation | Number of identical words | Probability of a randomly matched sequence |
|---|---|---|---|---|---|
| gb\|M88725\| | SPARR16SE | Spirochaeta zuelzeri 16S ribosomal RNA. | | 289 | 9.0e-17 |
| gb\|M71237\| | TRPRR16SB | Treponema pectinovorum 16S ribosomal... | | 263 | 1.3e-13 |
| gb\|M57739\| | TRPRRDSC | Treponema phagedenis 16S rRNA. | | 244 | 1.0e-11 |
| gb\|M57737\| | TRPRRDSA | Treponema bryantii 16S rRNA. | | 239 | 3.0e-11 |
| gb\|M71236\| | TRPRR16SA | Treponema denticola 16S ribosomal RNA. | | 235 | 7.0e-11 |
| gb\|M59294\| | TRPSSRNAA | Treponema sp. small subunit ribosomal... | | 232 | 1.3e-10 |
| gb\|M88720\| | SPARR16SA | Spirochaeta isovalerica 16S ribosomal rRNA | | 222 | 1.1e-09 |

(B)

```
                    +---------Spa16sa
               +--6 +
               !    +---------M06b8_Un
          +--7 !
          !    !    +--Trprnaa
          !    !    +--5
          !    +--4 +--Trpdsa
     +--3 !    !
     !    !    !         +---Trp16sb
     !    !    +---------+
     !    !              +---------Spa16se
+--2 !    !
!    !    +---2 !
!    !         +--1 !
!    !              +---------Trprsc
!    !
!    +-----------------------Trprrl
+--1 !
     !      +---------M06b8_Un
     !      !
     +---7  !  +--Trprnaa
     !    !  +--5
     !    +--4 +--Trpdsa
     !    !
     !    !    +--Spa16sa
     !    +--6
     !         +--Spa16se
     !
+--3 +--Trprsc
!
!
+--Trprrl
```

```
                 1
   Trprrl6sa    AGGGAATGCT TCTTTGATGA CGGTAGTCAT GCGAATAAGC CCCGGCTAAT
   Trprrdsc     AGGGAATGCG TCCTTGATGA CGGTAGTCGA GCGAATAAGC CCCGGCTAAT
   Sparrl6se    AGGGAATGAC ATCATGATGA CATTAGTCG. GTGAATAAGC CCCGGCTAAC
   Trprrl6sb    AGGGAATGGT ATAGAGGTGA CAGTAGGTAA .TGAATAAGC ACCGGCTNAT
   Trprrdsa     AGAGAAACGC TTTGTGGTGA CTGTAGGTCA .TGAATAAGC AACGGCTAAT
   Trpssrnaa    AGGGAATGGC CCCGCGGTGA CTGTAGGTCT .AGAACAAGC ACCGGCTAAT
   Sparrl6sa    AGGTAATGAC RGTYAGATGA CGTTAGCTTA .TGAATAAGC TCCGGCCAAT
   M06b8_Univ   .......... ......GTAG CAGTCACCGG TACACCCAAT GCATGCCCTA 51
   Trprrl6sa    TACGTGCCAG CAGCCGCGGT AACACGTAAG GGNNNAGCGT TGTTCGGAAT
   Trprrdsc     TACGTGCCAG CAGCCGCGGT AACACGTAAG GGGNNAGCGT TGTTCGGAAT
   Sparrl6se    TACGTGCCAG CAGCCGCGGT AACACGTAGG GGGCNAGCGT TGTTCGGAAT
   Trprrl6sb    TACGTGCCAG CAGCCGCGGT NACACGTAAG GTGCCAGCGT TATTCGGAAT
   Trprrdsa     TACGTGCCAG CAGCCGCGGT AACACGTAAG TTGCGAGCGT TGTTCGGAAT
   Trpssrnaa    TACGTGCCAG CAGCCGCGGT AACACGTAAG GTGCTAGCGT TGTTCGGAAT
   Sparrl6sa    TACGTGCCAG CAGCCGCGGT AACACGTAAG GAGCGAGCGT TGTTCGGAAT
   M06b8_Univ   GAGCAGCCAC GCGCCAGGTA GAACTGCAAA TCGCTCGGAC CGTGTCGGAA 101
   Trprrl6sa    TATTGGGCGT AAAGGGTATG TAGGCGGTTA GGTAAGCCTG GTGTGAAATC
   Trprrdsc     TATTGGGCGT AAAGGGCACG CAGGCGGGTT GGTAAGCCTG NTGTGAAATA
   Sparrl6se    TATTGGGCGT AAAGGGCATG TAGGCGGTTT GGTAAGCCTG GTGTGAAATC
   Trprrl6sb    TATTGGGCGT AAAGGGCACG CAGGCGGTTA TGCAAGCTTG GTGTGAAATA
   Trprrdsa     TATTGAGCGT AAAGGGCATG TAGGCGGTTC TGCAAGTCTG GTGTGAAATG
   Trpssrnaa    TATTGGGCGT AAAGGGCATG TAGGCGGCGC GATAAGTCAG ACGTGAAATC
   Sparrl6sa    TATTGGGCGT AAAGGGCATG TAGGCGGTTT TGTAAGTCTG GTGTGAAATA
   M06b8_Univ   TATTG.GCGT AAAGGGCATG TAGGCGGCTA TGTAAGCCTG ATGTGAAATC 151
   Trprrl6sa    TACGAGCTCA ACTCGTAAAC TGC.ATTGGG TACTGC.TTG ACTTGAATCA
   Trprrdsc     CTCAAGCTTA ACTTGAGAAT TGC.ATTGGG TACTGC.CAG TCTTGAATCA
   Sparrl6se    CTGCAGCTTA ACTGTAGAAT TGC.ATTGGG TACTGC.CAG ACTTGAATCA
   Trprrl6sb    CTGGGGCTTA ACCCCAGAAC TGC.ATTGAG AACTGC.AAG ACTAGAGTCA
   Trprrdsa     CCGGGGCTCA ACCCCGGAAC TGC.GTTGGA AACTGC.AGA ACTTGAGTCG
   Trpssrnaa    CCGGGGCTCA ACCCCGGAAC TGC.GTTTGA TACTGT.TGC GCTTGAGTCA
   Sparrl6sa    CTACAGCTTA ACTGTGGGAA CGC.ACTGGA AACTGT.GAG ACTAGAATCA
   M06b8_Univ   CTGGGGCTTA ACCCTAGAAT AGCAATTGGG TACTGTATAG CCTTGAATTA 201
   Trprrl6sa    CGGAGGGGAA ACCGGAATTC CAAGTGTAGG GGTGGAATCT GTAGATATTT
   Trprrdsc     CGGAGGGGAA ACCGGAATTC CAAGTGTAGG GGTGGAATCT GTAGATATTT
   Sparrl6se    CAGAGGGGAA ACTAGAATTC CAGGTGTAGG GGTGGAATCT GTAGATATCT
   Trprrl6sb    GTGAGGGGAA ATCGGAATTC CAGGTGTAGG GGTGAAATCT GTAGATATCT
   Trprrdsa     CTGAGGGGCN GCCAGAATTC CAGGTGTAGG GGTGAAATCT GTAGATATCT
   Trpssrnaa    GCGAGGCGGA ACCGGAATTC CTGGTGTAGG GGTGAAATCT GTAGATATCA
   Sparrl6sa    GTGAGGGGTA ACCGGAATTC CTTGTGTAGG GGTGAAATCT GTTGATATAA
   M06b8_Univ   CGGAAGGGAA CTGGATCAGT ACCCATTTAG ACTGAATCAC GTA.......
```

FIG. 7B

METHOD FOR RAPID IDENTIFICATION OF PROKARYOTIC AND EUKARYOTIC ORGANISMS

This is a continuation of application Ser. No. 08/203,056 filed on Feb. 28, 1994 abandoned.

FIELD OF THE INVENTION

The present invention relates to the field of taxonomy. More specifically, it presents a new method for obtaining DNA sequence data that can be used to assign an unknown species. This method can also be used to monitor the representation of different species in a mixed population, since it has broad specificity for a wide assortment of organisms.

BACKGROUND OF THE INVENTION

Taxonomic classification of organisms requires the study of both the similarities and differences between the organisms. Genetic homology and mutations are analogous to the morphological criteria that have classically been used to deduce evolutionary relationships. Nucleic acid sequences of equivalent (orthologous) genes in different species are now used to determine taxonomic relationships between the species (Woese, C. R.,1987, Microbial. Rev., 51, pp 221–271).

Taxonomic assignment plays an important role in medical and industrial research. It allows for identification of organisms (either unicellular or multicellular) based on comparison of a DNA sequence from the unknown organism with orthologous sequences from other organisms. The identification is done by taxonomic assignment of this sequence on a phylogenetic tree based on the entire set of orthologous sequences.

In industrial microbiology, taxonomic assignment can allow classification of organisms that carry out chemical reactions. The catalytic process in such reactions can often be recognized by knowing what type of organism carried it out. In medicine, such assignment can diagnose the infectious agents or to identify the type of organism that synthesizes one or more pharmacological agents. In environmental science, taxonomic assignments of the organisms in the ecosystem are useful in preparing environmental impact statements, since changes in its composition can be rapidly identified by determining the DNA sequences of the organisms present.

By the way of background, the current methods of molecular taxonomic assignments involve the sequencing of long segments (several thousand base pairs) of genomic ribosomal DNA (rDNA) or ribosomal RNA. The comparison of the sequences obtained with the sequences of other known species allows their classification. This approach can be tedious and time consuming due to the difficulties in obtaining long DNA sequences. The methodology of the invention offers a rapid way of obtaining the sequence data to carry out the taxonomic analysis. This novel approach has several advantages over the prior art. The Applicant's method involves selection, and then polymerase chain reaction (PCR) amplification of a phylogenetically-informative DNA fragment from an unknown organism. The sequence of this fragment provides sufficient information to make a taxonomic assignment. This approach has broad specificity and is less likely, than existing methods, to fail to identify an unknown organism. This method can identify new variants that arise by mutation or natural selection (i.e. the proliferation of new strains), since the oligonucleotide primers in this invention (hereby called universal primers) are designed to retrieve sequences that are less specific than others which are specifically designed to amplify a particular species or group of species. A single assay can be performed to identify many different organisms.

The Applicant's invention presents a novel method of identifying universal primers to amplify DNA with the PCR. This method is less costly than methods requiring the preparation of unique PCR primers designed to amplify one or limited number of species. By taking advantage of the exquisite sensitivity of PCR, the present invention utilizes extremely small quantities of material to identify the specimen. An additional advantage of the invention is that it does not require culturing of the organism prior to running the test. This is particularly important for those organisms which are currently impossible to grow outside of a host, or those which require special conditions for their propagation. The PCR amplification products can be cloned and sequenced, or sequenced directly after purification. Multiple organisms in a mixture can be discriminated if the PCR products are cloned. Since the present method exhibits broad specificity, it can therefore be useful in monitoring the representation of different eukaryotic or prokaryotic species in an ecosystem over time and space.

SUMMARY OF THE INVENTION

In accordance with the present invention, a new method for obtaining data for molecular taxonomic assignment is presented. A highly polymorphic region of genomic DNA, flanked on both sides by adjacent conserved DNA sequences, is searched for to design universal primers, which are used to amplify the entire genomic region by PCR. Subsequent DNA sequencing of the amplified polymorphic region allows taxonomic assignment of this DNA sequence by molecular phylogenetic comparison with other known sequences.

The present method is based on the fact, that by comparing corresponding gene sequences from three or more organisms, one can deduce relationships which can be used for biological classification. Portions of a gene with the greatest number of differences (defined as polymorphism) generally produce the largest amount of useful data for classification of new specimens. Nearly all organisms (unicellular and multicellular) contain ribosomal RNA. This DNA template is particularly useful in classifying living organisms. Orthologous ribosomal RNA sequences from various organisms are displayed as a sequence logo in order to identify highly polymorphic regions. In this representation, the height of letters measures the degree of sequence conservation among several species. A region which has two conserved motifs surrounding a highly variable domain is selected. The conserved portions are similar in many organisms, and can be used to design oligonucleotides that will be complementary to these sites regardless of the organism. PCR is used to amplify the taxonomically informative polymorphic domain using the universal primers. The amplified DNA is sequenced and when sequences are compared to other known sequences, these amplified pieces of DNA will allow the organism to be classified phylogenetically.

The present invention applies an information analysis used in the past by T. S. Schneider and R. M. Stephens (1990, Nucl. Acids Res., Vol. 18, pp 6097–6100) to identify regulatory sequence elements controlling the expression of adjacent genes. The authors proposed a graphical method for displaying the patterns in a set of aligned sequences. From this "sequence logo" one can determine not only the consensus sequence but also the relative frequency of each base and the information content (measured in bits) at every position in a site or sequence. The logo displays both significant residues and subtle sequence patterns. The logo was originally developed to study DNA binding sites recognized by proteins. These sequences are usually quite short (less than 30 nucleotides). In contrast, the current application represents the first known application of information analysis in molecular taxonomy. The sequences presented in this invention are the longest known logos to date. The invention presented here demonstrates a new use of the sequence logo to design universal PCR primers. The primers represent a set of degenerate nucleotide sequences, in which set the presence of a particular nucleotide in the primer is proportional to the frequency this nucleotide is present in the sequence logo (expressed in bits). The degenerate sequences contrast with those used to retrieve genes based on the genetic code for amino acid sequences, since ribosomal DNA does not have protein coding function, and thus the ambiguities inherent in the genetic code are not applicable to taxonomy based on ribosomal DNA. These degenerate sequences are not obvious and cannot be identified by other existing methods. They are representative of the total set of orthologous ribosomal DNA sequences rather than the consensus sequence, since the consensus is really the mode of the multiply aligned starting set of ribosomal DNAs. This means that the consensus sequence is not likely to be as comprehensive as the universal primer in amplifying ribosomal DNA from organisms of unknown origin.

OBJECTS OF THE INVENTION

An object of this invention is to provide a novel method for providing data for molecular taxonomic assignment based upon obtaining a DNA sequence of a relatively short but highly polymorphic segment of genomic DNA.

Another object of this invention is to provide a method for designing universal primers for the amplification of the selected DNA segment, said primers being able to amplify genomic DNA from a wide range of organisms using the polymerase chain reaction technique.

It is also an object of this invention to provide a diagnostic kit for taxonomic assignment of the unknown species when a small sample of genomic DNA can be obtained. This and other objects and advantages of the present invention over the prior art, and a better understanding of the invention and its use will become readily apparent from the following description and are particularly delineated in the appended claims.

DESCRIPTION OF THE DRAWINGS

FIG. 1. Aligned sequences for part of the 28S rDNA from 9 eukaryotic species. Hum: (*Homo sapiens*, humans); Lem: (*Citrus limon*, lemon); Mrace: (*Mucor recemosis*, zygomycete, a fungus); Rice: (*Oryza saliva*, rice); Slime: (*Physarum polycephalum*, slime mold); Tom: (*Lycopersican esculentum*, tomato); Worm: (*Caenorhabditis elegans*, nematode, worm); Xlrn: (*Xenopus laevis*, South American toad); Yeast: (*Saccharomyces cerevisiae*, baker's yeast).

FIG. 6. DNA sequencing of PCR amplification product of 16S ribosomal sequences from two distinct Treponeme subspecies. Corresponding sequence intervals of the phylogenetically informative domain of the 16S rDNA PCR products are shown for *T. vincenti* and *T. denticola*.

FIG. 7A. Comparison of rDNA sequence of unknown, ancient pathogen (Mo6B8) with closely-related contemporary treponema, and spirochaete species. (A) Statistical likelihood of sequence identity between known and unknown sequences. (B) Equally parsimonious DNA phylogenies generated from multiple sequence alignment.

FIG. 7B. Multiple sequence alignment MO6B8 sequence with orthologous rDNA segments from treponeme and spirochaetes.

DETAILED DESCRIPTION OF THE INVENTION

Figure 2:
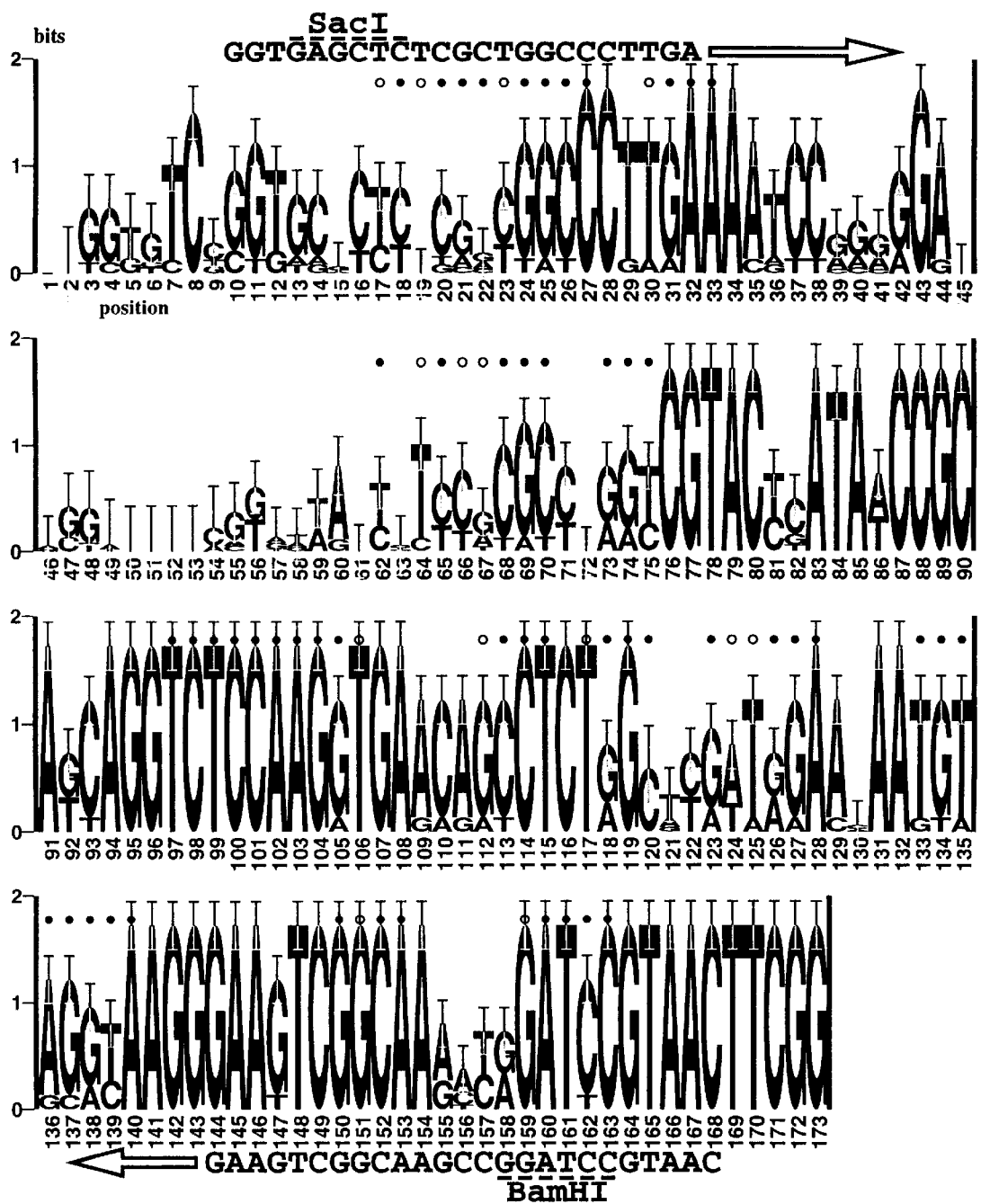
FIG. 2. Sequence logo created from the sequences shown in FIG. 1. The horizontal axis represents the position of nucleotides in the alignment; these correspond to FIG. 1. The vertical axis represents information (sequence conservation) in bits. Error bars indicate the standard deviation of the height of each stack. This represents the expected variation of the conservation due to the small (finite) sample of aligned sequences. The coordinates of the left (SacI) primer is shown corresponding to the human sequence. The complement of the right (BamHI) primer is shown for clarity. The coordinates of the BamHI primer, (corresponding to the human sequence) on the other strand of DNA is found by switching A's with T's and C's with G's and writing the sequence backwards. The 5' and 3' terminal coordinates of the PCR product are orthologous to positions 2698 and 2849 of the human sequence (GenBank entry HUMRGM, accession number M11167). Proposed RNA structure in *X. laevis* 28S RNA is shown by paired bases (bullet) and G-U base pairs (open circle). Unmarked bases are single stranded.

If two different species have identical genes, then we have little to say about how they evolved from a common ancestor. When two genes differ at one or more sites, the number of nucleotide changes indicates how much the two organisms have diverged from a common ancestor. This invention describes a rapid method for identifying and then amplifying regions of sequence divergence.

All organisms employ ribosomes to carry out the important biological task of protein synthesis, so ribosomal subunits have been structurally and functionally conserved throughout the eons. The sequences of ribosomal RNAs from widely differing species can be aligned and then the differences between these sequences specify the evolutionary or phylogenetic relationships between the organisms.

Eukaryotic ribosomes contain several conserved RNAs, the largest of which is called the 28S ribosomal RNA (rRNA). In order not to bias the analysis to regions studied previously, we initially chose to use full length 28S sequences in the sequence alignment. Sequences having the broadest possible taxonomic distribution were selected in order to maximize species diversity. Sequences of plant, animal, fungal and protistan origin were used. The corresponding 28S ribosomal DNA (rDNA repository) sequences were aligned by a "rectification algorithm" (Feng D. F. et al., 1987, J. Mol. Evol., 25:351–360) in which the human sequence was chosen to be a reference sequence. The human sequence was aligned in a pairwise fashion with each of the other sequences, and then the modified reference sequence (containing gaps) was realigned with the other sequences again to produce the final alignment.

First, using the DNA data bank, regions of DNA that have similar features are located and used to align the sequences. DNA sequence regions that are similar in more than one species are said to be conserved. This conservation can be visualized with a sequence logo, which displays the nucleotides that are present in multiply aligned sequences. These logos can be used to locate a region of sequence divergence surrounded by two regions of conservation. Next DNA primers are designed which can anneal to the conserved regions in the polymerase chain reaction (PCR) amplification. The information analysis of logos, generates a set of degenerate nucleotide sequences, that are used to design the universal oligonucleotide primers for PCR amplification of a taxonomically-informative, intervening sequence. These primers allow for the amplification of both conserved regions to which they anneal, and the divergent DNA sequences between them. The amplified DNA is then sequenced and the sequence of the variable region can be used to construct dendrograms which depict the taxonomic relationships between different organisms.

This method simultaneously satisfies the requirement of PCR for two conserved DNA sequences from which to perform DNA amplification, and the requirement of taxonomy for a highly variable DNA region from which to construct evolutionary trees.

Figure 8:
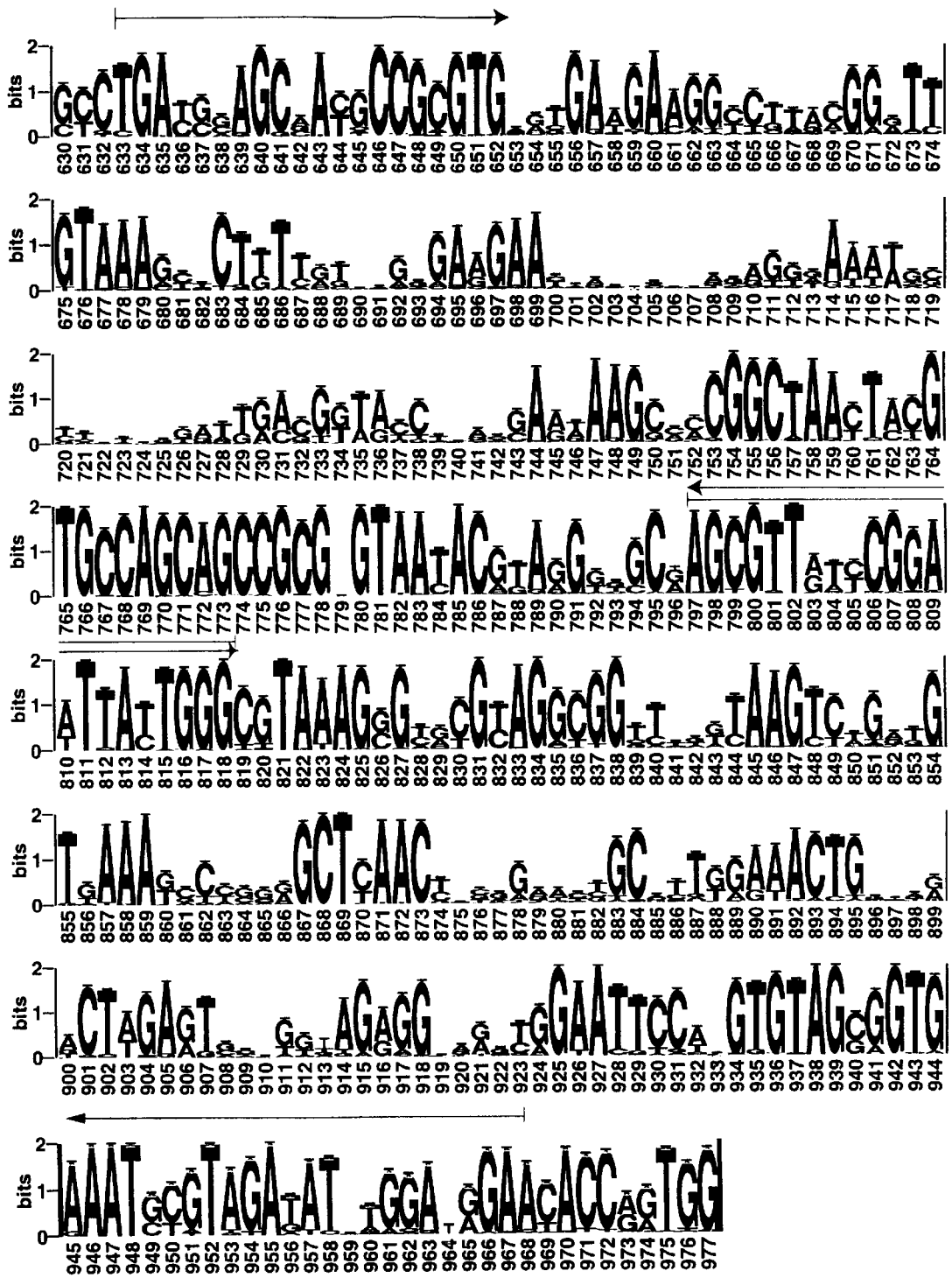
FIG. 8. Sequence logo of a 16S ribosomal DNA segment created from 55 prokaryotic full-length 16S rDNA sequences that were previously aligned by rectification. The horizontal axis represents the position of nucleotide in the complete 16S alignment. The vertical axis represents information (i.e. sequence conservation) in bits. Error bars indicate the standard deviation of the height of each stack. The oligonucleotide primer sequences for PCR amplification are depicted by arrows above the sequence symbols. The 5' amplification product (I) spans positions 634 through 819 of the logo. The 3' amplification product (II) begins at position 798 and extends to position 968. Note that (a) the nucleotides at the 3' end of each primer sequence are completely conserved (approximately 2 bits in height), which assures nearly universal amplification of a wide variety of prokaryotic species; (b) the interstitial sequences amplified by these primers are generally of limited information content; this sequence-specific variability between distant taxa correlates with the degree of phylogenetic relationship between these species.

Sequence logos (FIGS. 2 and 8) were prepared in several steps. Sequences were selected from highly divergent taxa to insure that the interval selected would be phylogenetically informative, and that the oligonucleotide primers would have close to universal specificity in the PCR amplification reaction. Initially, multiple 16S (in the case of prokaryotic species) or 28S (for eukaryotic species) rDNA sequences were aligned, then the information content was calculated at each position of the multiple alignment, and finally displayed in the form of a sequence logo. Multiple sequence alignment was carried out with the program PILEUP of the GCG sequence Analysis Software package (Devereux et al. 1984, Nucleic Acids Res., 12:387–395). Initially, the degree of similarity of each pair of sequences to be aligned is estimated by pairwise alignment. These relationships determine the clustering strategy for the multiple alignment. PILEUP first aligns the two most-related sequences to each other to produce the first cluster. The final alignment is created from a series of progressive, pairwise alignments between sequences and clusters of sequences. This is converted into a sequential format suitable for input to the computer program ALPRO of the DELILA software analysis package (Schneider et al. 1986, J. Mol. Biol., 188:415–431). ALPRO calculates the number of bits per nucleotide at each site in the alignment and the associated variance on this quantity. The computer program MAKELOGO displays the contribution of each nucleotide to the information content at each position on the alignment (Schneider and Stephens, 1990, Nucl. Acids Res., 18:6097–6100).

The total information content at each position is the basis for selecting phylogenetically-informative regions flanked by >18 bp segments showing sufficient sequence conservation to be used as primers for the PCR amplification reaction. The ratio of the number of bits of each nucleotide at each position to the total number of bits at that site determines the proportion of a particular nucleotide at degenerate sites in the oligonucleotide primer. A ratio of 0.05 is taken as the minimum proportion required to include this nucleotide in a degenerate site (see below). Otherwise, the primer is designed to be homogeneous at that position.

The consensus sequence of an aligned set of sequences is constructed by choosing the most frequent base at each position. Consensus sequences were not used to locate conserved and non-conserved regions because they are not quantitative, and they destroy data about the frequency of base occurrences. Because the sequence logo measures sequence conservation in a quantitative way, variable regions that may be useful in studying phylogeny can be rationally selected. The optimal universal PCR primer contains some degenerate sites, where no single nucleotide is present in all of the aligned sequences. The frequency of each nucleotide at each position in the oligonucleotide corresponds precisely with the number of bits of information contributed by that base at that position. This maximizes the ability of the primer to be complementary to the target sequences.

In summary, the sequence logo reveals evolutionary and, by inference, functional conservation of specific nucleotide sites in the ribosomal sequence. However, when applied in molecular phylogenetic analysis, it is simply a tool for assessing the most variable or conserved segments in the rDNA sequence. A highly variable domain flanked by highly conserved segments was identified in the sequence logo and the two conserved elements were used to design oligonucleotide primers for PCR amplification. Different sets of primers were shown to be suitable for amplification of taxonomically-informative regions in a wide variety of eukaryotes and prokaryotes (see examples). The DNA sequences of these PCR amplification products can be used to determine taxonomic relationships or to quickly place a previously unidentified species on the evolutionary tree.

EXAMPLE 1

Preparation of Sequence Logo

A sequence logo was created from the aligned 28S rDNA sequences, and the region shown in FIG. 1 was identified as having two conserved regions surrounding a divergent region. The horizontal axis represents nucleotide positions along the DNA, whereas the vertical axis measures the degree of conservation at the same position in the various species. The vertical scale is given in bits of information, which measures the number of choices between two equally likely possibilities. The choice of one base from the 4 possible bases requires two bits of information. The two bits correspond to two choices. For example, the first choice could determine whether the base is a purine or a pyrimidine and the second choice would specify which purine or pyrimidine is present. Thus, at position 100 of FIG. 1, all of the 28S sequences have a C so that position has two bits of conservation. In the logo (FIG. 2) a C appears at position 100 with a height of (almost) 2 bits. A small sample correction prevents it from being exactly 2 bits high (Schneider T. D. et al.,1986, J. Mol. Biol., 188:415–431). For those positions where two equally likely bases occur, there is only one bit of information. This is because a choice of 2 things from 4 is equivalent to a choice of 1 thing from 2. Position 86 is an example of this, in which 5 of the sequences contain A and 4 have T in FIG. 1. This position is therefore about 1 bit high in FIG. 2. The relative frequency of the bases determines the relative heights of the letters, and since A is more frequent, it is placed on top. Positions in which all four bases are equally likely are not conserved and so have zero heights on the logo. When the frequencies of the bases are other than 0, 50 or 100 percent, the heights still measure the conservation at each position, but the calculation is a bit more complicated. However, this method permits comparisons of the height of one position with any other.

EXAMPLE 2

Design of the Universal Primers

To be successful, the PCR technique requires the chemical synthesis of two closely-linked segments of DNA (which are referred to as primers). FIG. 2 shows the two primers for eukaryotic 28S rDNA, which were chosen after analysis of the sequence logo (see FIG. 1). The two PCR primers represent a set of oligomers in which set the frequency of a nucleotide is proportional to its presence at this particular position in the sequence logo. Primers were designed according to the following three criteria: (1) They are in regions of high conservation, and surround regions of low conservation. (2) The 3' termini cover regions that are invariant between species, so that the primer end which is extended by the DNA polymerase is always properly annealed to the DNA. (3) The oligonucleotide primers are not self complementary and do not base pair to each other. Because these primers were also designed to guarantee amplification of the human sequence, the 5' terminus of the left primer was not highly conserved. This had no effect on cross species amplification. The primers contain restriction sites useful for subsequent cloning of the amplification product. The primers cover DNA from base 10 through 168 (FIG. 1), so the amplified human product was predicted to be 159 base pairs long.

The following primers have been designed:

28S primer sequences: eukaryotes

SacI primer

5'p-$(G_{0.8}/C_{0.2})(G_{0.9}/T_{0.1})(T_{0.75}/G_{0.25})(G_{0.8}/A_{0.1}/T_{0.1})$ $(C_{0.8}/A_{0.1}/G_{0.1})$N $(C_{0.6}/T_{0.4})$ $(T_{0.6}/C_{0.4})(T_{0.5}/C_{0.5})$N$(C_{0.6}/T_{0.2}/G_{0.2})(G_{0.6}/A_{0.2}/C_{0.2})$N$(C_{0.6}/T_{0.4})$ $(G_{0.9}/T_{0.1})(G_{0.9}/A_{0.1})$ $(C_{0.9}/T_{0.1})$CCTTGAAA-OH3' (SEQ ID NO:1)

BamH1 primer

5'p-GTTACG$(G_{0.9}/A_{0.1})$ATC$(C_{0.5}/T_{0.5})(A_{0.5}/G_{0.5})(T_{0.45}/G_{0.45}/A_{0.1})$ $(T_{0.6}/C_{0.4})$ TTGCCGA$(C_{0.8}/A_{0.2})$TTCCC-OH3' (SEQ ID NO:2)

16S DNA primer sequences: prokaryotes

Set I Forward:

5'-TGA$(T_{0.5}/C_{0.5})(G_{0.6}/C_{0.4})$ $(G_{0.5}/C_{0.5})$ AGC $(A_{0.33}/G_{0.33}/C_{0.33})$ A $(T_{0.5}/C_{0.5})$ GCCGCGTG-3 (SEQ ID NO:3)

Reverse:

5'-CCCA$(A_{0.7}/G_{0.3})$TAA$(T_{0.7}/A_{0.3})$TC CG$(A_{0.5}/G_{0.5})$ $(A_{0.7}/T_{0.3})(T_{0.5}/C_{0.5})$AACGC-3' (SEQ ID NO:4)

Set II Forward:

5'-GCGTT(A0.5/G0.5)(A0.3/T0.7)(T0.5/C0.5) CGGA (T0.3/A0.7)TTA(T0.7/C0.3)TGGG-3' (SEQ ID NO:5)

Reverse:

5'-TC$(T_{0.4}/C_{0.6})$NT$(C_{0.95}/G_{0.05})(C_{0.95}/T_{0.05})(A_{0.8}/T_{0.2})$ NAT$(A_{0.9}/C_{0.1})$TCTAC $(G_{0.7}/A_{0.3})(C_{0.6}/G_{0.4})$ATT-3' (SEQ ID NO:6)

wherein the subscripts represent the relative abundance of the corresponding nucleotide at that position in the sequence. This abundance is determined by information analysis of a large (>50) number of multiply-aligned rDNA sequences from a wide variety of eukaryotic or prokaryotic species.

EXAMPLE 4

PCR Amplification

The following conditions were used for PCR amplification: 10 ng to 100 ng of genomic DNA was incubated with 20 pmol of each primer, in buffer supplemented with $MgCl_2$ (1.5 mM), KCl (25 mM) 0.05% Tween 20, 100 µg/ml of BSA, and 50 µM of each dNTP. 1 unit of Taq DNA polymerase (Perkin Elmer Cetus) was used in a 50 µl reaction volume. After incubation of oligonucleotide universal primers and genomic DNA for 4' at 94 degrees C., 40 cycles were performed at 94 degrees C., 1'; 55 degrees C., 1'; 72 degrees C., 2' followed by a synthesis step (72 degrees C.,7'). The annealing temperature is usually optimized experimentally for unknown samples, since the degenerate sequences in the primer preclude the precise determination of the melting temperature of the oligo-template duplexes. The PCR products are separated on a 4% Nusieve agarose gel (Seakem). The gel is stained with ethidium bromide and photographed under ultraviolet light to visualize the amplicons.

Figure 3:
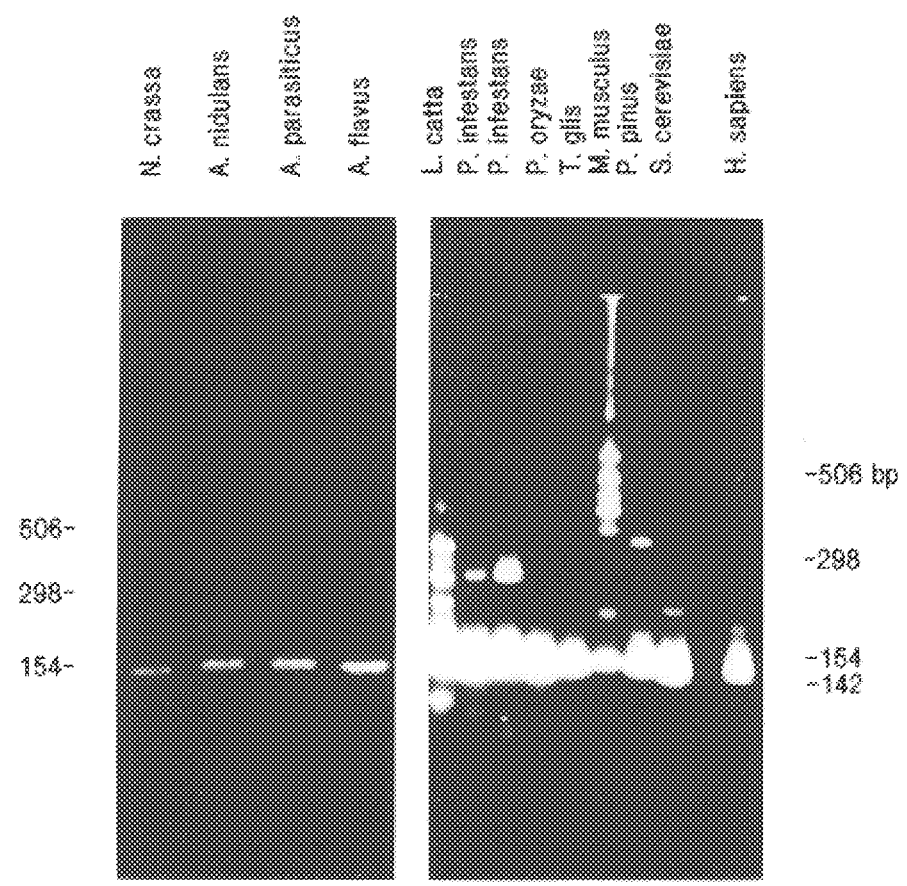
FIG. 3. PCR amplification reaction products generated with 28S rDNA universal primers. Reactions, (from left to right) are: *Neurospora crassa*, *Aspergillus nidulans*, *Aspergillus parasiticus*, *Aspergillus flavus* (fungal species), *Lemur catta* (brown lemur), *Phytophthora infestans* (Irish potato blight of 1840, strain 506), *Phytophthora infestans* (strain 10126), *Pyricularia oryzae* (rice blast fungus), *Tupaia glis* (tree shrew), *Mus musculus* (domestic mouse), *Pichia pinus* (a soil fungus), *Saccharomyces cerevisiae* (baker's yeast), and *Homo sapiens*.
Figure 4:
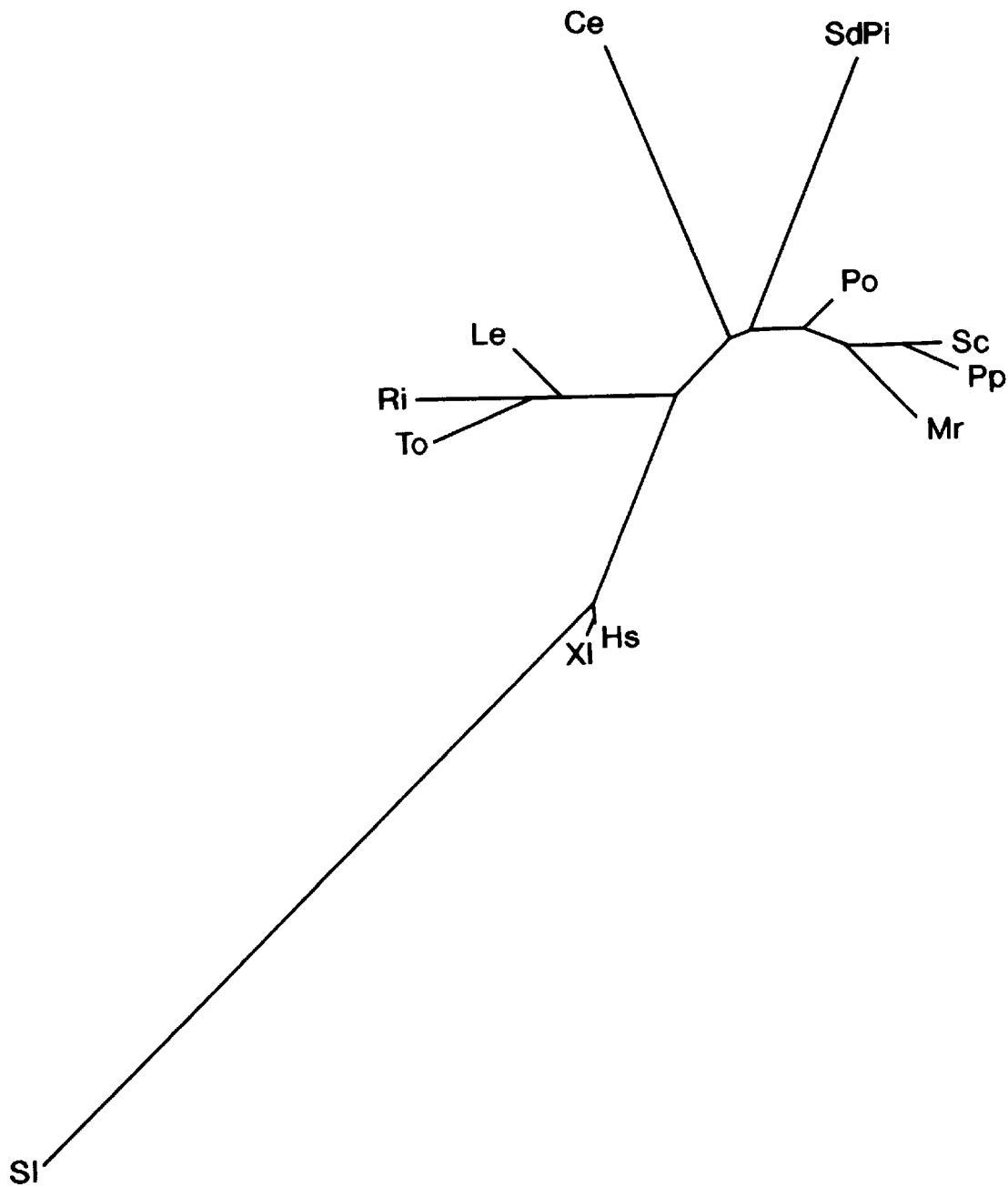
FIG. 4. Molecular phylogeny showing taxonomic relationship of *P. infestans* (Pi) and *P. pinus* (Pp) rDNA sequences amplified with universal primers. PCR amplification products from these organisms digested with SacI and BamHI, cloned into pUC8, and sequenced by the dideoxy chain termination method. The sequences were aligned with other publicly available sequences; *S. cerevisiae* (Sc), *M. racemosis* (Mr), *P. oryzie* (Po), *C. elegans* (Ce), *X. laevis* (Xl), *H. sapiens* (Hs), *P. polycephalum* (Si), tomato (To), rice (Ri), and lemon (Le), by a rectification algorithm. A majority rule consensus tree derived from the 25 Fitch-Margoliash distance matrix trees was constructed from the alignment. As expected, the *P. pinus* sequence occurs on the same branch as the other ascomyceate sequence, *S. cerevisiae*. The *P. infestans* sequence cluster with the rDNA sequence of the dinoflagellate, *Prorocentrum micans* (Sd), rather than the fungal sequences. In contrast with the nearly all fungal species, *P. infestans* develops a swimming stage during its life cycle. Classical taxonomy studies have recently suggested that *P. infestans* may be more closely related to the brown algae (which contain the dinoflagellate group), which also have swimming stage. The molecular phylogeny based on using universal primer amplified PCR products supports this revised taxonomic assignment.
Figure 5:
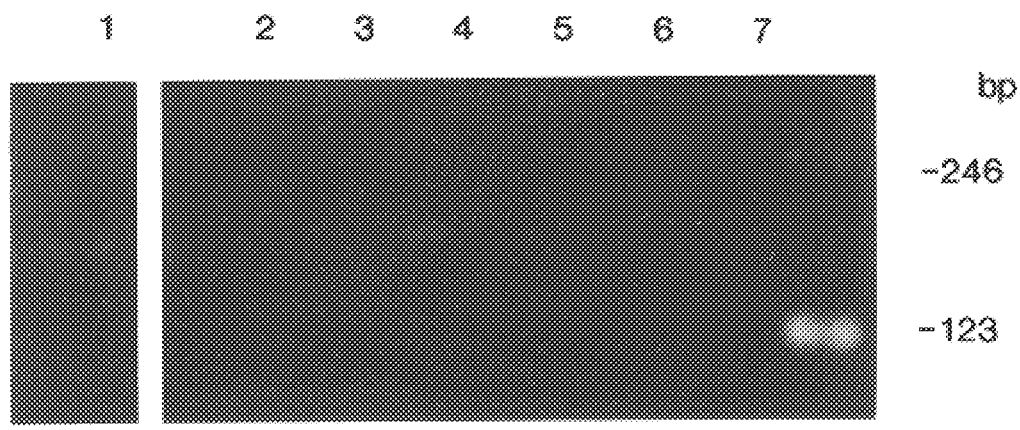
FIG. 5. Polymerase chain reaction (PCR) of different bacterial species with universal prokaryotic oligonucleotide primers. The predicted PCR product spans a 205 bp interval (beginning and terminating at position 225 and 430) within the 16S rDNA gene. PCR products were separated on 4% NuSieve agarose gels and photographed. Information analysis was used to identify primer sequences in a multiple sequence alignment generated from ribosomal DNA sequences of 35 distinct prokaryotic organisms. Lanes: 1—*Chlamydia trachomatis*, 2—*T (reponema) pallidum*, 3—*T. pertenue*, 4—*T. refringens*, 5—*T. denticola*, 6—*T. vincenti*, 7—*T. phagedenis*. Molecular size markers are shown in base pairs.

When PCR reactions were carried out on genomic DNA purified from 12 different organisms, a major product was observed in each case (FIG. 3). Except for *H. sapiens*, none of the species tested were included in the original sequence alignment. This result demonstrates that the universal primers can be applied to PCR amplification of DNA from other species. To illustrate the broad specificity of the universal primers, a number of mammalian species were amplified as well as several different classes of fungi. The diverse set of fungal species that were successfully tested is particularly significant, as ribosomal sequences within this subkingdom show a high degree of DNA sequence diversity. The DNA sequences of the cloned DNA segments from *H. sapiens, M. musculus,* and *S. cerevisiae* amplification products were determined and found to correspond precisely with published reports of those sequences. This shows that amplification was of high fidelity, as well as broad specificity, and that contaminating genomic templates were not present. The phylogenetic relationships inferred from the 28S sequences of the other species were generally compatible with the known taxonomic relationships between these organisms.

Minor amplification products were observed in several of these reactions (*L. catta, P. infestans, M musculus, P. pinus* and *S. cerevisiae* lanes). The fragments may have arisen from amplification at sites within these genomes which happen to be complementary to our primers. This possibility is, in part, a function of the annealing temperature of the PCR reaction, which was deliberately chosen to be permissive for amplification of rDNA from a wide variety of extant species. Alternatively, since organisms have many copies of the 28S gene, some of these may have large variations in the amplified regions. In particular, the region selected for amplification of 28S is adjacent to a target sequence which is commonly interrupted by a site-specific transposable element in some organisms. Thus the evolutionary instability of this region of the 28S gene may give rise to variants which, upon amplification, could produce these minor species-specific PCR products. These artifacts do not interfere with subsequent isolation, cloning and sequencing of the desired products because the desired products do not co-migrate with the artifacts on the gel used to purify them.

EXAMPLE 4

Sequencing of the Amplified DNA

The sequencing was performed according to the standard method of Sanger and Nicklen 1975 (dideoxy method).

EXAMPLE 5

Identification of Treponema in ancient DNA samples

Multiple hypotheses have been advanced to explain the origin of treponematosis and its worldwide dispersion. Paleopathological studies have suggested treponematosis as the most likely cause for the epidermal and spongiform bone lesions commonly seen in preserved, pre-Columbian, South American human remains. Although the spirochaetes responsible for pinta, yaws, endemic syphilis, and venereal syphilis display substantial antigenic overlap, the ribosomal DNA (rDNA) sequences of each of these pathogens are unique. The objective of this study was to retrieve ancient prokaryotic rDNA sequences to identify, if possible, the etiologic agent(s) of the infection in preserved, mummified remains manifesting ancient treponematosis. Nucleic acids were extracted from soft tissues (muscle) of 4 individuals with evidence of tertiary treponematosis excavated from sites at El Morro, Arica (Chinchorro culture) and San Miguel de Azapa (Gentilar culture), Chile. Control amplifications with a polymerase chain reaction procedure demonstrated the recovery of ancient human DNA in each specimen. Prokaryotic PCR products were obtained for 2 of these Chinchorro individuals, both of which were excavated from the same cemetery. The prokaryotic universal primers were employed in the PCR amplification. The amplified DNA was cloned and sequenced using standard methods. A comparison of cloned ancient bacterial rDNA sequences against all known sequences revealed that 8 of the 10 most similar contemporary relatives were classified as spirochaetes, with 5 of these belonging to the genus Treponema. Sequences derived from two different individuals were nearly identical, suggestive of a similar infectious agent. None of the sequences were identical to the ancient isolates. The degree of similarity between the contemporary treponemal species was analogous to that found for the ancient sequences (78–85%). Attempts to amplify 2 different contemporary *T. pallidum* structural genes were unsuccessful, consistent with the possibility either that the ancient and contemporary sequences represent distinct species or that mutations in these genes have occurred which abrogate annealing of the oligonucleotide primers to the ancient template. Other cloned sequences were similar to *Spiroplasma* species as well as potential agents of decomposition. Phylogenetic analysis of the ancient rDNA sequence suggests the closest association with *T. phagedenis, T. denticola, S. zuelzerae* and *T. pallidum* rather than other Spirochaetes. These results suggest that ancient treponematosis in Chile may have been due to a spirochaete similar, but not identical, to *T. pallidum*.

This invention can be used as basis for a kit for retrieval of phylogenetically informative DNA sequences. This kit would contain all of the components of the polymerase chain reaction and the universal oligonucleotide primers.

Thus, while a preferred embodiment of the invention is illustrated and described, it is to be understood that this invention is capable of variation and modification. The invention is not intend to be limited to the precise terms set forth, but rather to be adaptable to various usages and altered conditions. Accordingly, such changes and alterations are properly intended to be within the full range of equivalents and, therefore, within the purview of the following claims. The terms and expressions which have been employed in the foregoing specification are used therein as terms of description and not of limitation, and thus there is no intention in the use of such terms and expressions of excluding equivalents of features shown and described or portions thereof, it being recognized that the scope of the invention is defined and limited only by the claims which follow.

Thus is described my invention and the manner and process of making and using it in such full, clear, concise, and exact terms so as to enable any person skilled in the art to which it pertains, or with which it is most nearly connected, to make and use the same.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Degenerate oligonucleotide
           sequence
           derived from analysis of information
           from a multiple sequence alignment of
           orthologous ribosomal RNA sequence ( i i i ) HYPOTHETICAL: no ( i v ) ANTI-SENSE: no ( x ) FEATURE:
        ( D ) OTHER INFORMATION: The proportionate representation
           of each nucleotide at a degenerate position corresponds
           to the frequency of this nucleotide at the corresponding
           position in the sequence alignment ( x i ) SEQUENCE DESCRIPTION: SEQ ID NO: 1:

SKKDVNYYYN BVNYKRYCCT TGAAA 25

( 2 ) INFORMATION FOR SEQ ID NO:2:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Degenerate oligonucleotide
           sequence derived from analysis of information
           from a multiple sequence alignment of orthologous
           ribosomal RNA sequence ( i i i ) HYPOTHETICAL: no ( i v ) ANTI-SENSE: no ( x ) FEATURE:
        ( D ) OTHER INFORMATION: The proportionate representation
           of each nucleotide at a degenerate position
           corresponds to the frequency of this nucleotide at the
           corresponding position in the sequence alignment ( x i ) SEQUENCE DESCRIPTION: SEQ ID NO: 2:

GTTACGRATC YRDYTTGCCG AMTTCCC 27

( 2 ) INFORMATION FOR SEQ ID NO:3:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Degenerate oligonucleotide
           sequence
           derived from analysis of information
           from a multiple sequence alignment of orthologous ribosomal RNA sequence ( i i i ) HYPOTHETICAL: no ( i v ) ANTI-SENSE: no ( x ) FEATURE:
( D ) OTHER INFORMATION: The proportionate representation
of each nucleotide at a degenerate position
corresponds to the frequency of this nucleotide at the
corresponding position in the sequence alignment ( x i ) SEQUENCE DESCRIPTION: SEQ ID NO: 3:

TGAYSSAGCV AYGCCGCGTG 20

( 2 ) INFORMATION FOR SEQ ID NO:4:

( i ) SEQUENCE CHARACTERISTICS:
( A ) LENGTH: 21 nucleotides
( B ) TYPE: nucleic acid
( C ) STRANDEDNESS: single
( D ) TOPOLOGY: linear ( i i ) MOLECULE TYPE: other nucleic acid
( A ) DESCRIPTION: Degenerate oligonucleotide
sequence
derived from analysis of information
from a multiple sequence alignment of orthologous
ribosomal RNA sequence ( i i i ) HYPOTHETICAL: no ( i v ) ANTI-SENSE: no ( x ) FEATURE:
( D ) OTHER INFORMATION: The proportionate representation
of each nucleotide at a degenerate position
corresponds to the frequency of this nucleotide at the
corresponding position in the sequence alignment ( x i ) SEQUENCE DESCRIPTION: SEQ ID NO: 4:

CCCARTAAWT CCGRWYAACG C 21

( 2 ) INFORMATION FOR SEQ ID NO:5:

( i ) SEQUENCE CHARACTERISTICS:
( A ) LENGTH: 21 nucleotides
( B ) TYPE: nucleic acid
( C ) STRANDEDNESS: single
( D ) TOPOLOGY: linear ( i i ) MOLECULE TYPE: other nucleic acid
( A ) DESCRIPTION: Degenerate oligonucleotide
sequence derived from analysis of information
from a multiple sequence alignment of
orthologous ribosomal RNA sequence ( i i i ) HYPOTHETICAL: no ( i v ) ANTI-SENSE: no ( x ) FEATURE:
( D ) OTHER INFORMATION: The proportionate
representation of each nucleotide at a degenerate
position corresponds to the frequency of this
nucleotide at the corresponding position in the
sequence alignment ( x i ) SEQUENCE DESCRIPTION: SEQ ID NO: 5:

GCGTTRWYCG GAWTTAYTGG G 21

( 2 ) INFORMATION FOR SEQ ID NO:6:

( i ) SEQUENCE CHARACTERISTICS:

-continued

```
      ( A ) LENGTH: 22 nucleotides
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: Degenerate oligonucleotide
            sequence derived from analysis of information
            from a multiple sequence alignment of orthologous
            ribosomal RNA sequence ( i i i ) HYPOTHETICAL: no ( i v ) ANTI-SENSE: no ( x ) FEATURE:
      ( D ) OTHER INFORMATION: The proportionate representation
            of each nucleotide at a degenerate position corresponds
            to the frequency of this nucleotide at the corresponding
            position in the sequence alignment ( x i ) SEQUENCE DESCRIPTION: SEQ ID NO: 6:

T C Y N T S Y W N A  T M T C T A C R S A  T T                                    2 2
```

What is claimed is:

1. A method of obtaining data for taxonomic assignment of unknown species comprising:

(a) searching for a divergent segment of DNA with low average information content determined quantitatively surrounded by two conserved segments of said DNA with high average information content determined quantitatively;

(b) designing primers for PCR amplification of said divergent segment by constructing a sequence logo for said DNA such that said primers contain a set of sequences present in said sequence logo that encompass the nucleotide variability of said conserved segments, which primers can anneal to said conserved segments;

(c) amplifying said divergent segment of DNA by PCR technique using said primers;

(d) sequencing the amplified DNA; and (e) comparing the resulting sequences with previously known sequences to determine the most similar related sequences.

2. The method of claim 1, wherein the searching for said divergent segment of DNA surrounded by said conserved segments is performed in the region of the DNA coding for the ribosomal RNA of any organism.

3. The method of claim 2, wherein said ribosomal RNA is the 28S ribosomal RNA from eukaryotic organisms or the 16S ribosomal RNA from prokaryotic organisms.

4. Primers for amplification of the DNA coding for 28S ribosomal RNA from eukaryotic organisms comprising:

SacI primer:
   5'p-$(G_{0.8}/C_{0.2})$ $(G_{0.9}/T_{0.1})$ $(T_{0.75}/G_{0.25})$ $(G_{0.8}/A_{0.1}/T_{0.1})$ $(C_{0.8}/A_{0.1}/G_{0.1})$ N $(C_{0.6}/T_{0.4})$ $(T_{0.6}/C_{0.4})$ $(T_{0.5}/C_{0.5})$ N $(C_{0.6}/T_{0.2}/G_{0.2})$ $(G_{0.6}/A_{0.2}/C_{0.2})$ N $(C_{0.6}/T_{0.4})$ $(G_{0.9}/T_{0.1})$ $(G_{0.9}/A_{0.1})$ $(C_{0.9}/T_{0.1})$ CCTTGAAA-OH3' (SEQ ID NO:1)

BamH1 primer:
   5'p-GTTACG $(G_{0.9}/A_{0.1})$ATC$(C_{0.5}/T_{0.5})$ $(A_{0.5}/G_{0.5})$ $(T_{0.45}/G_{0.45}/A_{0.1})$ $(T_{0.6}/C_{0.4})$TTGCCGA$(C_{0.8}/A_{0.2})$ TTCCC-OH3' (SEQ ID NO:2)

wherein the subscripts represent the relative abundance of the corresponding nucleotide at that position in the sequence as determined by information analysis of a large number of multiply-aligned sequences from a wide variety of eukaryotic species.

5. Primers for amplification of the DNA coding for 16S ribosomal RNA from prokaryotic organisms comprising:

SetI Forward:
   5'-TGA$(T_{0.5}/C_{0.5})$ $(G_{0.6}/C_{0.4})$ $(G_{0.5}/C_{0.5})$ AGC $(A_{0.33}/G_{0.33}/C_{0.33})$A $(T_{0.5}/C_{0.5})$ GCCGCGTG-3 (SEQ ID NO:3)

Reverse:
   5'-CCCA$(A_{0.7}/G_{0.3})$ TAA $(T_{0.7}A_{0.3})$ TC CG$(A_{0.5}/G_{0.5})$ $(A_{0.7}/T_{0.3})$ $(T_{0.5}/C_{0.5})$AACGC-3' (SEQ ID NO:4)

SetII Forward:
   5'-GCGTT $(A_{0.5}/G_{0.5})$ $(A_{0.3}/T_{0.7})$ $(T_{0.5}/C_{0.5})$ CGGA $(T_{0.3}/A_{0.7})$TTA$(T_{0.7}/C_{0.3})$TGGG-3' (SEQ ID NO:5)

Reverse:
   5'-TC$(T_{0.4}/C_{0.6})$NT$(C_{0.95}/G_{0.05})$ $(C_{0.95}/T_{0.05})$ $(A_{0.8}/T_{0.2})$NAT$(A_{0.9}/C_{0.1})$TCTAC $(G_{0.7}/A_{0.3})$ $(C_{0.6}/A_{0.4})$ ATT-3' (SEQ ID NO:6)

wherein the subscripts represent the relative abundance of the corresponding nucleotide at that position in the sequence as determined by information analysis of a large number of multiply-aligned sequences from a wide variety of prokaryotic species.

* * * * *